United States Patent [19]

Reiling

[11] 4,224,933

[45] Sep. 30, 1980

[54] SEXUAL STABILIZER AND STIMULATOR

[75] Inventor: Joseph W. Reiling, 112 Miller Ave., Battle Creek, Mich. 49017

[73] Assignee: Joseph William Reiling, Battle Creek, Mich.

[21] Appl. No.: 949,621

[22] Filed: Oct. 10, 1978

[51] Int. Cl.² .......................... A61F 5/00; A61H 19/00
[52] U.S. Cl. .................................................... 128/79
[58] Field of Search ......................... 128/79, 24 R, 67

[56] References Cited

U.S. PATENT DOCUMENTS

| D. 246,117 | 10/1977 | Okamoto | 128/79 |
|---|---|---|---|
| 1,608,806 | 11/1926 | Nelson | 128/79 |
| 2,018,328 | 10/1935 | Smith | 128/79 |
| 3,131,691 | 5/1964 | Scott | 128/79 |

FOREIGN PATENT DOCUMENTS

| 476413 | 5/1929 | Fed. Rep. of Germany | 128/79 |
|---|---|---|---|
| 554178 | 7/1932 | Fed. Rep. of Germany | 128/79 |
| 23165 | 12/1900 | United Kingdom | 128/79 |

*Primary Examiner*—Lawrence W. Trapp

[57] ABSTRACT

A sexual stabilizer and stimulator worn on a penis for exciting both partners of a sex act; the device including a tubular sleeve of thin latex, constrictions at opposite end portions thereof, several stiffening stays imbedded in the sleeve extending longitudinally, a zig-zagged row of balls tethered on the outer side of the sleeve, and a band adjustably attached to straps near a base end of the sleeve.

2 Claims, 6 Drawing Figures

U.S. Patent    Sep. 30, 1980    4,224,933
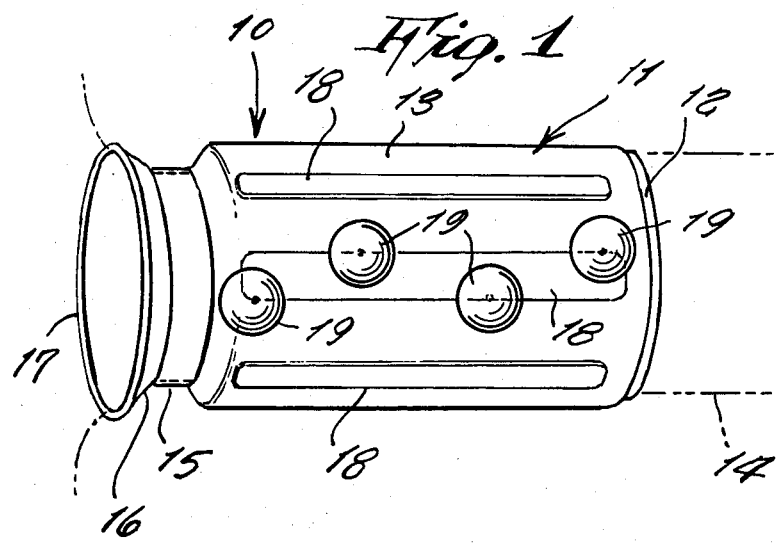
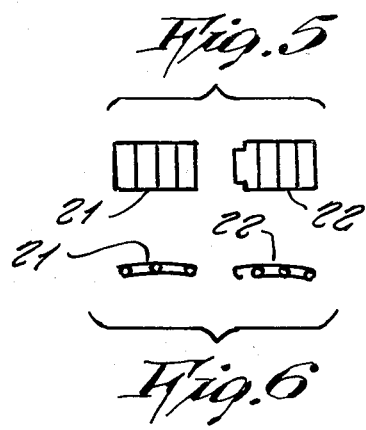
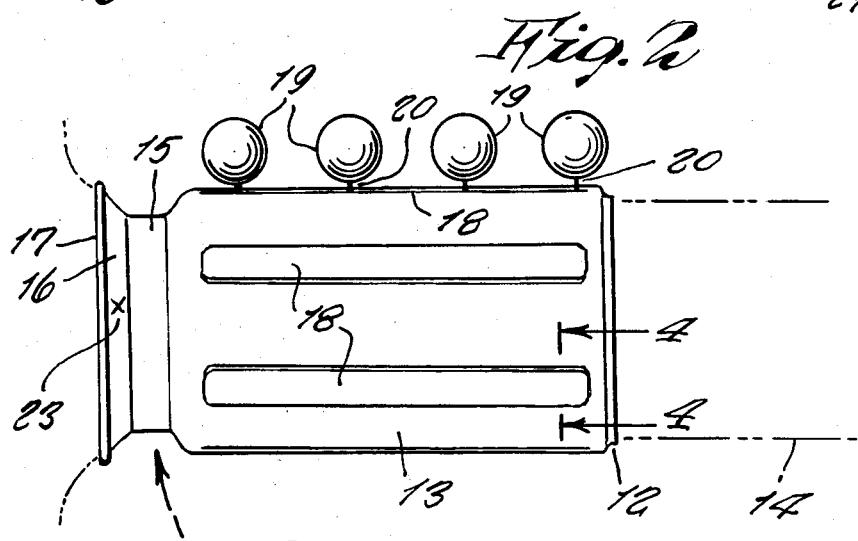
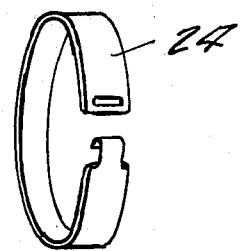
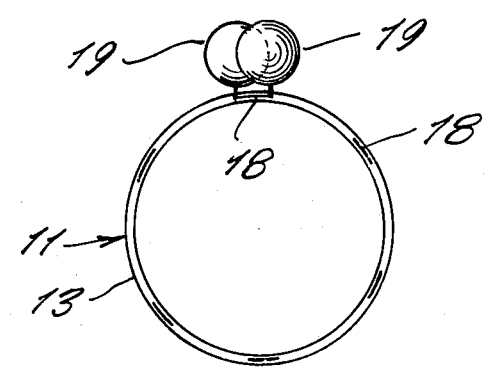

SEXUAL STABILIZER AND STIMULATOR

This invention relates generally to devices termed as sex aids. More specifically, it relates to sex act stimulating devices.

It is generally well known that a great percentage of women do not find fulfillment during a sex act. Also, men often find themselves hard pressed to maintain an erection during the act. Thus, many married couples, in time, feel that they are sexually incompatible, and it is a proven fact, from surveys made, that the greater percentage of divorces stem directly from a lack of sexual compatability. This serious situation is, accordingly, in want of a solution.

Therefore, it is a principal object of the present invention to provide a device that sexually stimulates both persons during the sex act, so as to overcome the above-indicated conditions, and improve a married couple's life.

Another object is to provide a sexual stabilizer and stimulator, that makes possible penetration, where, otherwise, penetration would be impossible.

Yet another object is to provide a sexual stabilizer and stimulator, which will aid in completely overcoming frigidity in women.

Yet a further object is to provide a sexual stabilizer and stimulator, which is, in no way, harmful to either party of a sex act.

Yet a further object is to provide a sexual stabilizer and stimulator, which will, in most cases, prolong the male's ability to act.

Other objects are to provide a sexual stabilizer and stimulator, which is simple in design, inexpensive to manufacture, rugged in construction, easy to use and efficient in operation.

These, and other objects, will be readily evident, upon a study of the following specification, and the accompanying drawing, wherein:

FIG. 1 is a top perspective view of the invention, shown full scale, and illustrated including a stretchable rubber band molded in the restriction collar near the left end;

FIG. 2 is a side elevation view thereof, and showing a modified construction, in which the stretchable rubber band is of separate snap-on type;

FIG. 3 is a front end view thereof, shown diagrammatically;

FIG. 4 is an enlarged cross-sectional view through one of the stays, showing it to be imbedded within the latex film material;

FIG. 5 is a top view of adjustable strap members that are fastened to the stimulator, and FIG. 6 is a side view thereof.

Referring now to the drawing in greater detail, the reference numeral 10 represents a sexual stimulator, according to the present invention, wherein there is a tubular body 11, made of stretchable, surgical latex or other soft, equivalent material, which is approximately one-sixteenth inch. The body is about three and one-half inches long, and approximately one and three-fourths inches in diameter. A forward end portion 12 of the body is one-sixteenth inch less in diameter than the body long, main portion 13. The end portion 12 keeps the same snugly on the penis 14, even when flaccid.

A diametrically restricted portion 15, at the other end of the main portion 13, is of thicker material, and is one-fourth inch wide, while being three-sixteenths inch less in diameter than the main portion, so as to grasp firmly around the base end of the penis. A terminal end portion 16, adjacent the restricted portion flared outwardly, and has a rolled over edge 17.

While specific dimensions have been indicated for the body, it may be manufactured in other sizes, so as to accommodate all wearers.

From five to seven stays 18, depending on stimulator diameter size, are imbedded within the main portion of the body. The stays, made of semi-rigid plastic, are flat, with all corners rounded, so as not to pierce the body.

A row of one-half inch diameter, smooth, soft balls 19, located outside of the body 11, are attached to one of the stays 18 by a stem 20, that is only one-thirty second inch long, in order to allow the balls a limited sway in any direction. Each alternate ball is attached to opposite side edges of the stay, as shown, and may be either of plastic or rubber.

Adjustable strap members 21 and 22 may be incorporated into the body construction, by affixing each, at its one end, to diametrically opposite sides of the terminal end portion 16, as shown at 23, and the opposite ends of the straps being adjustably attachable to opposite ends of a rubber, thread-like band 24, placeable behind the testicles.

In operative use, the restricted area of the device gently limits the flow of blood from the penis, due to a slight, harmless pressure on this organ at the organ base. The blood, therefore, stays in the penis, creating and helping to maintain a normal, natural erection. The extra blood supply also causes the nerve endings in the penis to be super-sensitive, thus producing unbelievable sensations during the sex act. The rolled over edge is used to enable the user to pull the device into position on the penis, which should be back against the body. When in place, the two rows of balls will center on top of the penis. The light-weight stays keep the device from rolling up the penis, when in use. The restricted area also functions to keep the device from sliding off the penis, while in use. To further insure the device's staying in place, the rubber, thread-like band can be made a part of the unit, and it then can be placed behind the testicles, but as a rule, this is not needed. The device stays in position quite well without it. During the act, the balls massage the clitoris of the female, thus creating pleasant sensations which the male organ is incapable of producing by itself, and thus completely satisfying the female.

When the device is used without the balls, it becomes a stabilizer.

What I now claim is:

1. A sexual stabilizer and stimulator, comprising, in combination, a tubular sleeve of thin surgical latex, a constriction at opposite ends of a main portion thereof, means for maintaining a penis erect even when flaccid, and means to excite the female partner of a sex act; the first said means comprising a plurality of thin, spaced-apart stays embedded in said main portion; and the second said means comprising a row of soft balls tethered to an outer side of said sleeve.

2. The combination as set forth in claim 1, wherein securement means attached to said sleeve include a pair of straps and a band.

* * * * *